(12) United States Patent
Behrens et al.

(10) Patent No.: US 7,829,129 B2
(45) Date of Patent: Nov. 9, 2010

(54) METHOD TO REDUCE CORROSION DURING FERMENTATION OF MICROALGAE

(75) Inventors: Paul W. Behrens, Ellicot City, MD (US); John M. Thompson, Baltimore, MD (US); Kirk Apt, Ellicot City, MD (US); Joseph W. Pfeifer, III, Reisterstown, MD (US); James P. Wynn, Columbia, MD (US); James Casey Lippmeier, Columbia, MD (US); Jaouad Fichtali, Lexington, KY (US); Jon Hansen, Lexington, KY (US)

(73) Assignee: Martek Biosciences Corporation, Columbia, MD (US)

( * ) Notice: Subject to any disclaimer, the term of this patent is extended or adjusted under 35 U.S.C. 154(b) by 210 days.

(21) Appl. No.: 11/738,416

(22) Filed: Apr. 20, 2007

(65) Prior Publication Data

US 2008/0032354 A1 Feb. 7, 2008

Related U.S. Application Data

(60) Continuation of application No. 11/313,524, filed on Dec. 20, 2005, now Pat. No. 7,252,979, which is a division of application No. 10/957,075, filed on Oct. 1, 2004, now Pat. No. 7,163,811.

(60) Provisional application No. 60/508,505, filed on Oct. 2, 2003.

(51) Int. Cl.
*C11B 1/00* (2006.01)
*C12N 1/12* (2006.01)
*A23D 9/00* (2006.01)
*C12P 7/64* (2006.01)

(52) U.S. Cl. .............. 426/417; 435/257.1; 435/134; 426/601

(58) Field of Classification Search ................. 426/417, 426/601; 435/257.1, 134
See application file for complete search history.

(56) References Cited

U.S. PATENT DOCUMENTS 5,130,242 A 7/1992 Barclay (Continued)

FOREIGN PATENT DOCUMENTS

JP 07-075556 3/1995

(Continued)

OTHER PUBLICATIONS

Aqua Craft.RTM., Inc., Issue No. 3, The Facts About Instant Ocean. RTM., http://www.aquacraft.net/w0014. html, .COPYRGT. 2000, printed on Jan. 6, 2006.

(Continued)

*Primary Examiner*—Karen Cochrane Carlson
*Assistant Examiner*—Rosanne Kosson
(74) *Attorney, Agent, or Firm*—Sterne, Kessler, Goldstein & Fox P.L.L.C.

(57) ABSTRACT

Methods for production of highly unsaturated fatty acids by marine microorganisms, including the heterotrophic marine dinoflagellate *Crypthecodinium*, using low levels of chloride ion are disclosed. Specifically, methods of increasing production of highly unsaturated fatty acids by marine microorganisms while growing in low chloride media by manipulating sodium ion and potassium ion levels. The invention also relates to methods of production of highly unsaturated fatty acids by marine organisms at low pH levels, and includes methods for generation of low pH tolerant strains.

18 Claims, 2 Drawing Sheets

U.S. PATENT DOCUMENTS

| | | | |
|---|---|---|---|
| 5,397,591 | A | 3/1995 | Kyle et al. |
| 5,407,957 | A | 4/1995 | Kyle et al. |
| 5,492,938 | A | 2/1996 | Kyle et al. |
| 5,711,983 | A | 1/1998 | Kyle et al. |
| 6,410,281 | B1 | 6/2002 | Barclay |
| 6,566,123 | B1 | 5/2003 | Barclay |
| 7,163,811 | B2 | 1/2007 | Behrens et al. |
| 7,252,979 | B2 | 8/2007 | Behrens et al. |
| 2001/0016342 | A1 | 8/2001 | Higashiyama et al. |
| 2008/0032352 | A1 | 2/2008 | Behrens et al. |
| 2008/0032353 | A1 | 2/2008 | Behrens et al. |
| 2008/0032355 | A1 | 2/2008 | Behrens et al. |
| 2008/0032356 | A1 | 2/2008 | Behrens et al. |
| 2008/0032357 | A1 | 2/2008 | Behrens et al. |
| 2008/0032358 | A1 | 2/2008 | Behrens et al. |
| 2008/0032359 | A1 | 2/2008 | Behrens et al. |
| 2008/0044865 | A1 | 2/2008 | Behrens et al. |
| 2008/0044866 | A1 | 2/2008 | Behrens et al. |
| 2008/0166780 | A1 | 7/2008 | Barclay |

FOREIGN PATENT DOCUMENTS

| | | | |
|---|---|---|---|
| JP | 2000-60587 A | | 2/2000 |
| WO | WO 98/29558 A1 | | 7/1998 |
| WO | WO 01/53512 | | 7/2001 |
| WO | WO 01/76385 | | 10/2001 |
| WO | WO 01/76715 | | 10/2001 |
| WO | WO 2005/035775 | | 4/2005 |

OTHER PUBLICATIONS

Beach et al.; Environmental Influences on the Docosahexaenoate Content of the Triacylglycerols and Phosphatidylcholine of a Heterotrophic, Maine Dinoflagellate. *Crypthecodinium cohnii*; Biochimica et Biophysica Aeta; (1973); 316:56-65.

de Swaaf ME, et al., Analysis of docosahexaenoic acid biosynthesis in *Crypthecodinium cohnii* by 13C labelling and desaturase inhibitor experiments, J Biotechnol. Jun. 12, 2003;103(1):21-9.

de Swaaf ME, et al., Fed-batch cultivation of the docosahexaenoic-acid-producing marine alga *Crypthecodinium cohnii* on ethanol, Appl Microbiol Biotechnol. Mar. 2003;61(1):40-3. Epub Dec. 24, 2002.

De Swaaf ME, et al., High-cell-density fed-batch cultivation of the docosahexaenoic acid producing marine alga *Crypthecodinium cohnii*, Biotechnol Bioeng. Mar. 20, 2003;81(6):666-72.

de Swaaf ME, et al., Optimisation of docosahexaenoic acid production in batch cultivations by *Crypthecodinium cohnii* J Biotechnol. 1999 70:185-92.

Home; "Marine Chemistry Chapter 5: Elemental Composition of the Seas and Salinity Variations"; Wiley-Interscience; (1969); pp. 151-155.

Jiang et al.; "Effects of Salinity on Cell Growth and Docosahexaenoic acid content of the Heterotrophic Marine Microalga *Crypthecodinium cohnii*," J Industrial Microbiol & Biotechnol; (1999); 23(6):508-513.

Jiang et al.; Effects of Medium Glucose Concentration and pH on Docosahexaenoic Acid Content of Heterotrphic *Crypthecodinium cohnii*; Process Biochemistry ; (2000); 35:1205-1209.

Sijtsma L and de Swaaf ME, Biotechnological production and applications of the omega-3 polyunsaturated fatty acid docosahexaenoic acid, Appl Microbiol Biotechnol. Apr. 2004;64(2):146-53. Epub Jan. 22, 2004.

Stein; "Handbook of Phycological Methods" Cambridge University Press; (1973):33.

Tuttle et al.; An Optimal Growth Medium for the Dinoflagellate *Crypthecodinium cohnii*; Phycologia; (1975): vol. 14(1):1-8.

Vazhappilly et al.; "Eicosapentaenoic Acid and Docosahexaenoic Acid Production Potential of Microalgae and Their Heterotrophic Growth"; Journal of the American Oil Chemists Society, (1998) vol. 75, No. 3 p. 393-397.

International Search Report for International (PCT) Patent Application No. PCT/US04/32383, mailed Jan. 31, 2005.

Written Opinion for International (PCT) Patent Application No. PCT/US04/32383, mailed Jan. 31, 2005.

International Preliminary Report on Patentability for International (PCT) Patent Application No. PCT/US04/32383, issued Apr. 3, 2006.

Barrette et al., "Development of bacterial contamination during production of yeast extracts," Applied and Environmental Microbiology 65(7):3261-3263, 1999.

Fermentation Process Development of Industrial Organisms, Neway, ed., Marcel Dekker/CRC Press, Boca Raton, 1989, pp. 244-246.

BD Bionutrients Technical Manual, 3d ed., http://www.bd.com/ds/technicalCenter/index.asp, 2006, 4 pages.

Wang, J., et al., "Effects of Environmental Conditions on Growth and DHA Yield of *Crypthecodinium cohnii*," Marine Sciences 26(2):62-65, China Academic Journal Electronic Publishing House, CN (2002), Abstract only.

English language translation of Wang, J., et al., "Effects of Environmental Conditions on Growth and DHA Yield of *Crypthecodinium cohnii*," (2002) (Document NPL1).

English language translation of the Notice of Reasons for Rejection for Japanese Patent Appl. No. 2006-534148, mailed Mar. 29, 2010.

METHOD TO REDUCE CORROSION DURING FERMENTATION OF MICROALGAE

CROSS REFERENCE TO RELATED APPLICATIONS

This application is a continuation of U.S. patent application Ser. No. 11/313,524, filed Dec. 20, 2005, which is a divisional of U.S. patent application Ser. No. 10/957,075, filed Oct. 1, 2004, now U.S. Pat. No. 7,163,811, which claims the benefit of priority under 35 U.S.C. §119(e) from U.S. Provisional Application Ser. No. 60/508,505, filed Oct. 2, 2003. Each of the above-identified patent applications is incorporated herein by reference in its entirety.

FIELD OF THE INVENTION

This invention generally relates to methods for production of highly unsaturated fatty acids by marine microorganisms using modified amounts of chloride and potassium ion in the culture medium. More specifically, the invention is directed to a process for producing high levels of docosahexaenoic acid (DHA) by culturing marine microalgae, including the heterotrophic marine dinoflagellate, *Crypthecodinium*, in fermentors under non-corrosive conditions which includes culturing in a low chloride ion and a high potassium ion environment. This invention also relates to methods for production of highly unsaturated fatty acids, including DHA, by marine microorganisms at low pH levels.

BACKGROUND OF THE INVENTION

The beneficial effects of increased dietary intake of long chain omega-3 fatty acids in humans has been well documented, which includes the reduction of cardiovascular and inflammatory diseases (i.e. arthritis and atherosclerosis), reduction of depression, increasing length of gestation in the third trimester, and inhibiting tumor growth. Several heterotrophic marine microorganisms have been found to produce high levels of these important essential fatty acids, including that of genus *Crypthecodinium* (Jiang and Chen, Process Biochemistry 35 (2000) 1205-1209; Jiang and Chen, Journal of Industrial Microbiology & Biotechnology, (1999) Vol. 23, 508-513; Vazhappilly and Chen, Journal of the American Oil Chemists Society, (1998) Vol. 75, No. 3 p 393-397; Kyle, U.S. Pat. Nos. 5,407,957; 5,397,591; 5,492,938; and 5,711,983).

*Crypthecodinium cohnii* is one of the most desirable organisms to utilize for the production of DHA (C22:6n-3), one of the most important long chain omega-3 fatty acids. *C. cohnii* is advantageous because DHA is the only polyunsaturated fatty acid (PUFA) produced by this organism in appreciable quantities. Other organisms produce two or more polyunsaturated fatty acids (PUFAs) in their lipids, and the complexity of their lipid profile can limit the use of their oils in some food and pharmaceutical applications (e.g. due to the presence of other undesirable PUFAs in the oil or due to ratios of the different PUFAs falling out of the desirable range for the specific application). In the marine environment, *Crypthecodinium cohnii* is usually found in full salinity seawater and, as such, is adapted to growth in an environment with a high chloride concentration. In fact, most cultures in published research on *C. cohnii* show that the growth and DHA production does best at salinities greater than about 20% of seawater (Jiang and Chen). The chloride ion concentration equivalent to 20% seawater is about 3870 ppm chloride ion or 3.87 g/l chloride ion. (Home 1969).

Tuttle and Loeblich (1975) developed an optimal growth medium for *C. cohnii*. The disclosed medium contained a sodium chloride concentration of 342 millimolar (mM). The equivalent grams per liter of sodium ion and chloride ion in a 342 mM sodium chloride solution are 7.86 g/L sodium ion and 12.12 g/L of chloride ion.

Beach & Holz (1973) reported that when culturing *C. cohnii* over a range of NaCl concentrations (0.3%, 1.8% and 5.0% (1.82 g/l, 10.9 g/l and 30.3 g/l chloride ion, respectively)) lipid yield (expressed as mg per $10^9$ cells) declined as NaCl concentrations decreased. Lipid yield at 0.3% NaCl was approximately one third of that at 5.0% NaCl.

More recently, Jiang and Chen (1999) determined the effects of salinity on cell growth and DHA content with three strains of *Crypthecodinium cohnii* and found in all cases that the optimum growth rates for cells and DHA yields were between 5 g/L and 9 g/L sodium chloride, which corresponds to 3.0 and 5.5 g/L chloride ion, respectively.

The natural chloride concentration of seawater (19,353 ppm, or 19.35 g/l chloride ion) (Home 1969, page 151) promotes corrosion in stainless steel fermentors. For example, of the two common grades of stainless steel used in manufacturing fermentors, 304-stainless steel is susceptible to corrosion when the chloride level exceeds 300 ppm (0.3 g/l chloride ion), and 316-stainless steel is susceptible to corrosion when the chloride level exceeds 1000 ppm (1 g/l chloride ion). Other grades of stainless steel exist that are more resistant to chloride corrosion, but they are extremely expensive and generally only used in fermentation equipment employed for the production of very expensive compounds.

Although it may be predicted that minimizing corrosion of stainless steel fermentors may be achieved by lowering chloride concentrations in the culture medium, in practice this is not an easy task. Marine microalgae, which are derived from the sea, generally require a certain amount of chloride ion, preferably as sodium chloride, to maintain growth and lipid production when grown in culture.

However, attempts to date to grow marine microalgae at low chloride concentrations while maintaining levels of production of omega-3 polyunsaturated fatty acids such as DHA have been unsuccessful. Jiang and Chen (1999) were unable to demonstrate significant DHA yields at NaCl levels less than 5 g/L, corresponding to a chloride level of about 3033 ppm or 3 g/L.

U.S. Pat. No. 6,410,281, issued Jun. 25, 2002, to Barclay, provides a method for growing euryhaline organisms such as *Thraustochytrium* sp. and *Schizochytrium* sp. in low chloride media by substituting non-chloride sodium salts to replace the sodium lost when lowering sodium chloride levels.

There exists a need for a process which would enable the production of a high yield of DHA from *Crypthecodinium cohnii*, while inhibiting or preventing corrosion in the most commercially desirable production vessels, stainless steel culture fermentors. This process would have to enable effective growth of the microorganism in a medium containing preferably less than 300 ppm chloride. Three hundred ppm chloride represents a level 10-18 times lower than the lowest chloride levels demonstrated by Jiang & Chen (1999) to be the best for the production of strains of *Crypthecodinium*.

Another desirable characteristic of microbial fermentations is the ability to grow cells at low pH (less than or equal to about pH=5.0) to inhibit the growth of bacteria in fungal fermentations. However, the literature indicates that *Crypthecodinium* grows best at a neutral pH (about pH 7). Tuttle and Loeblich in *Phycologia* Vol. 14(1) 1-8 (1975), disclose that the pH optimum for *Crypthecodinium* growth is 6.6, with growth being "very slow" below pH 5.5. There exists a need for strains and/or methods of growing *Crypthecodinium* at low pH while retaining normal growth and production of DHA.

SUMMARY OF THE INVENTION

In attempting to minimize sodium chloride levels in culture medium for *Crypthecodinium*, where sodium chloride leads to the problem of corrosion of fermentors, the inventors have surprisingly discovered that sodium chloride levels can be reduced by manipulation of the sodium and preferably the potassium salts in the culture medium to compensate for the decrease of chloride ion (down to 300 ppm or 0.3 g/L chloride ion) while maintaining the yield of DHA similar to what is obtained at about 4.5 g/L NaCl (corresponding to 2.73 g/l chloride ion).

The present inventors have identified culture conditions that allow *Crypthecodinium* to be grown in medium with substantially lowered chloride levels (down to about 0.3 g/l chloride ion) without adversely affecting the dry weight, fat content or DHA content when compared to growth in a normal "high chloride" medium. Attaining a comparable DHA yield was not merely a matter of replacing the sodium chloride in the medium with other sodium salts. In fact, replacement of sodium chloride with an equivalent amount of sodium from other sodium salts (i.e. sodium sulfate) did not result in a DHA yield comparable to the high chloride control case, but actually resulted in a further decrease in the DHA yield of the culture. Instead the present inventors surprisingly found that the best DHA yield was obtained when the potassium concentration (relative to that in seawater at 4.5 g/l NaCl or 17% of seawater) was significantly increased. It is unexpected that a substantial decrease in the amount of sodium and an increase in potassium concentration would be effective in compensating for a reduction in the chloride content of the medium.

In one embodiment, the present invention includes a method for producing docosahexaenoic acid (DHA) by culturing heterotrophic microalgae of the class Dinophyceae in a culture medium. The medium comprises chloride ion at a concentration of less than or equal to about 2 g/l and potassium ion at a concentration of greater than or equal to about 0.25 g/l. In this embodiment, the microalgae produces at least about 0.04 g DHA per liter of 7 day culture. A 7 day culture generally has about $5\times10^6$ cells/ml or about $5\times10^9$ cells/liter. Therefore, a culture having about 0.2 g/l DHA at 7 days contains about 0.04 g DHA/$10^9$ cells. In a preferred embodiment, the microalgae is of the genus *Crypthecodinium*. A more preferred microalgae is *Crypthecodinium cohnii*. Preferably, the chloride ion concentration is less than or equal to about 1 g/l, even more preferably less than or equal to about 0.3 g/l. Preferably, the potassium ion is greater than or equal to about 0.4 g/l, and even more preferably is equal to or greater than about 0.8 g/l. Preferably, the source of potassium ion is potassium sulfate. In a preferred embodiment, the medium further comprises a source of sodium ion such that the sodium ion concentration is from about 1 g/l to about 8 g/l. More preferably, the sodium ion is from about 1.5 g/l to about 5 g/l. A preferred source of sodium ion is sodium sulfate. Included in the present invention is a biomass produced by this method.

In another embodiment, the present invention includes a method of producing DHA by culturing heterotrophic microalgae of the class Dinophyceae in a culture medium. The medium comprises chloride ion at a concentration of less than or equal to about 2 g/l, potassium ion at a concentration of greater than or equal to about 0.25 g/l and sodium ion present in a ratio of less than or equal to about 27:1 wt:wt sodium:potassium. In this embodiment, the microalgae produces at least about 0.2 g DHA per liter 7 day culture or 0.04 g DHA/$10^9$ cells. In a preferred embodiment, the microalgae is of the genus *Crypthecodinium*. A more preferred microalgae is *Crypthecodinium cohnii*. Preferably, the chloride ion concentration is less than or equal to about 1 g/l, even more preferably less than or equal to about 0.3 g/l. Preferably, the potassium ion is greater than or equal to about 0.4 g/l, and even more preferably is equal to or greater than about 0.8 g/l. Preferably, the source of potassium ion is potassium sulfate. The medium further comprises a source of sodium ion such that the sodium ion is present in the medium in a ratio of less than 27 times (by weight) the weight of the potassium ion (expressed as 27:1 sodium:potassium wt:wt.). In a preferred embodiment, the sodium:potassium ratio is less than about 15:1. More preferred is a sodium:potassium ratio of about 4:1. A preferred source of sodium ion is sodium sulfate. Included in the present invention is a biomass produced by this method.

The present inventors have also identified culture medium conditions and strains that allow *Crypthecodinium* to be grown in medium with substantially lowered pH levels, while still maintaining a commercially practical rate of growth and production of lipid, including DHA. In another embodiment, the present invention includes a method of producing DHA by culturing heterotrophic microalgae of the class Dinophyceae in a culture medium, wherein the culture medium has a pH of less than about 6, and wherein the microalgae produces at least about 0.04 g DHA/$10^9$ cells. The medium may further comprise chloride ion at a concentration of less than or equal to about 2 g/l, potassium ion at a concentration of greater than or equal to about 0.25 g/l and sodium ion present in a ratio of less than or equal to about 27:1 wt:wt sodium:potassium. In this embodiment, the microalgae produces at least about 0.04 g DHA/$10^9$ cells. In a preferred embodiment, the microalgae is of the genus *Crypthecodinium*. A more preferred microalgae is *Crypthecodinium cohnii*. In a preferred embodiment, the pH is less than or equal to about pH 5.5, more preferably is less than or equal to about 5.0, and even more preferably less than or equal to about 4.5. In a preferred embodiment, the medium further comprises chloride ion concentration at less than or equal to about 2 g/l, preferably less than or equal to about 1 g/l, even more preferably less than or equal to about 0.3 g/l. The medium also comprises potassium ion at concentrations greater than or equal to about 0.25 g/l, greater than or equal to about 0.4 g/l, and even more preferably is greater than or equal to about 0.8 g/l. Preferably, the source of potassium ion is potassium sulfate. In a preferred embodiment, the medium further comprises a source of sodium ion such that the sodium ion concentration is from about 1 g/l to about 8 g/l. More preferably, the sodium ion is from about 1.5 g/l to about 5 g/l. A preferred source of sodium ion is sodium sulfate. Included in the present invention is a biomass produced by this method.

The present invention also includes a method for the selection of a low pH tolerant heterotrophic microalgae of the class Dinophyceae, comprising subculturing said microalgae in low pH media until the yield of DHA is greater than or equal to about 0.04 g DHA/$10^9$ cells. In a preferred embodiment, the pH is less than or equal to about 6, is less than or equal to about 5, is less than or equal to about 4.5. Included in the present invention is microalgae and a biomass produced by this method.

These and other objects, features, and advantages of the invention will become apparent from the following best mode description, the drawings and the claims.

DESCRIPTION OF THE INVENTION

Figure 1:
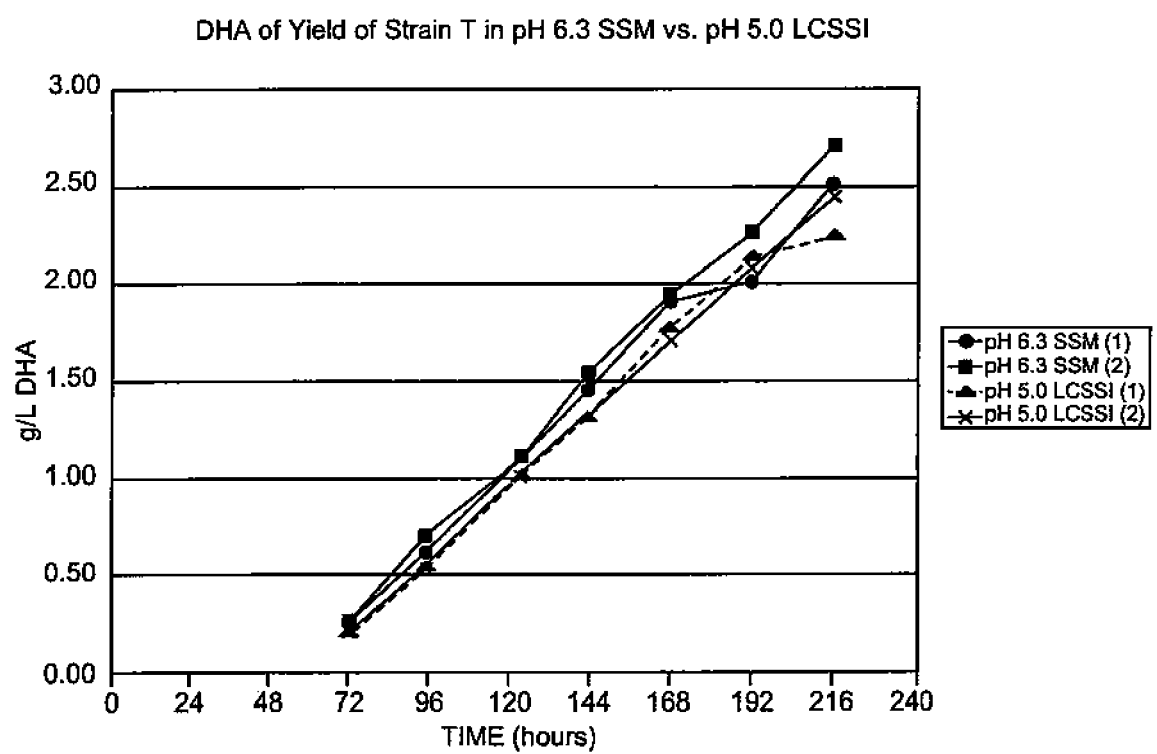
FIG. 1 is a graphical representation of a time course of DHA yield for duplicates of C. cohnii strain T-HF grown at pH 6.3 and 3 g/l chloride ion (denoted pH 6.3 SSM) and C. cohnii strain T-HF, adapted to low pH, grown at pH 5 and 1 g/l chloride ion (denoted pH 5.0 LCSSI).

The present invention solves the above-identified problem of corrosion of fermentors caused by high sodium chloride levels used for the growth of marine microalgae of the class Dinophyceae. The inventors have discovered culture media components which allow for commercially viable levels of growth of marine microalgae of the class Dinophyceae and production of DHA under low sodium chloride conditions, by using modified amounts of chloride and potassium ion in the culture medium. More specifically, the inventors have discovered that the loss of sodium caused by reducing sodium chloride to non-corrosive levels may be at least partially offset by increasing potassium levels in the culture media.

The present invention also solves the above-identified problem of allowing for growth of a marine microalgae of class Dinophyceae while simultaneously discouraging growth of bacteria. More specifically, the present invention provides methods to culture marine organisms such that they become tolerant to low pH. The present invention also provides strains of such microorganisms which are tolerant to low pH. Low pH-tolerant strains provided by the inventors can, at low pH levels, grow to cell densities and achieve DHA production levels comparable to that achieved by strains growing at more neutral pH levels. This is only one example of the technology encompassed by the invention, as the concepts of the invention can readily be applied to other production organisms and other desired PUFAs as described in detail below.

One embodiment of the present invention includes a method to produce docosahexanenoic acid (DHA) by culturing heterotrophic microalgae of the class Dinophyceae in a culture medium which includes the following components: chloride ion at a concentration of less than about 2 g/L, and potassium ion at a concentration of greater than about 0.25 g/L, where the microalgae produce at least about 0.2 g of DHA per liter of 7-day culture. The 7 day culture generally has $5 \times 10^6$ cells/ml resulting in about 0.04 g DHA/$10^9$ cells. In preferred embodiments, the heterotrophic microalgae produce at least about 0.04 g DHA/$10^9$ cells, at least about 0.06 g DHA/$10^9$ cells, at least about 0.08 g DHA/$10^9$ cells, at least about 0.10 g DHA/$10^9$ cells, at least about 0.12 g DHA/$10^9$ cells, at least about 0.14 g DHA/$10^9$ cells, at least about 0.16 g DHA/$10^9$ cells, at least about 0.18 g DHA/$10^9$ cells, at least about 0.20 g DHA/$10^9$ cells, at least about 0.22 g DHA/$10^9$ cells, at least about 0.24 g DHA/$10^9$ cells, at least about 0.26 g DHA/$10^9$ cells, at least about 0.28 g DHA/$10^9$ cells, or at least about 0.30 g DHA/$10^9$ cells. As used herein, reference to a nutrient concentration in a culture medium refers to the concentration of nutrients in the medium at the beginning of the step of culturing, which includes any nutrients carried over from previous stages in the process, such as preparation of an inoculum.

Microorganisms suitable for the present invention include heterotrophic microalgae, which include members of the class Dinophyceae (dinoflagellates). A preferred member of this class is a member of the genus Crypthecodinium. A preferred member of the genus Crypthecodinium is C. cohnii. Crypthecodinium cohnii is an obligate heterotroph requiring a reduced carbon source for growth, and contains a fatty acid profile in which DHA is the only polyunsaturated fatty acid present in appreciable quantities. Suitable organisms can be obtained from a number of publicly available sources, including by collection from the natural environment. For example, the American Type Culture Collection currently lists forty-five available strains of Crypthecodinium cohnii, identified as ATCC Nos. 30021, 30334-30348, 30541-30543, 30555-30557, 30571, 30572, 30772-30775, 30812, 40750, 50050-50060, and 50297-50300. As used herein, any microorganism, or any specific type of organism, includes wild strains, mutants, or recombinant types.

Apart from the sodium, chloride and potassium concentrations which are the subject of the present invention and discussed more fully below, other components of media of the present invention can be any components known in the art that promote the growth and production of DHA at commercially practicable levels, and include components such as those disclosed in U.S. Pat. Nos. 5,130,242, 5,407,957, 5,397,591; 5,492,938; and 5,711,983, all of which are incorporated by reference herein in their entirety. More specifically, a source of carbon, such as glucose, various starches, molasses, ground corn and the like may be used. A source of assimilable organic or inorganic nitrogen is also included in the culture media. Nitrogen sources may include nitrate, urea, ammonium salts, amino acids and the like. A source of assimilable phosphorous may also be provided. The medium also may contain a source of microbial growth factors, which are unspecified or specified compounds that enhance the heterotrophic growth of unicellular microorganisms, and may include yeast or other extracts, soil extracts, and the like. Specific examples of growth media for C. cohnii and related organisms, for example, may also be found in Jiang and Chen, Process Biochemistry 35 (2000) 1205-1209; Jiang and Chen, Journal of Industrial Microbiology & Biotechnology, (1999) Vol. 23, 508-513; Vazhappilly and Chen, Journal of the American Oil Chemists Society, (1998) Vol. 75, No. 3 p 393-397. Specific examples of preferred media to use with the present invention may be found in, for example, the Examples section herein below.

In one aspect of the media of the present invention, chloride ion concentrations are present in a concentration of less than or equal to about 2000 ppm or about 2 grams per liter of culture, more preferably less than or equal to about 1.9 g/l, more preferably less than or equal to about 1.8 g/l, more preferably less than or equal to about 1.7 g/l, more preferably less than or equal to about 1.6 g/l, more preferably less than or equal to about 1.5 g/l, more preferably less than or equal to about 1.4 g/l, more preferably less than or equal to about 1.3 g/l, more preferably less than or equal to about 1.2 g/l, more preferably less than or equal to about 1.1 g/l, more preferably less than or equal to about 1.0 g/l, more preferably less than or equal to about 0.9 g/l, more preferably less than or equal to about 0.8 g/l, more preferably less than or equal to about 0.7 g/l, more preferably less than or equal to about 0.6 g/l, more preferably less than or equal to about 0.5 g/l, more preferably less than or equal to about 0.4 g/l, and most preferably less than or equal to about 0.3 g/l. In alternative embodiments, the minimum chloride concentration is at least about 0.025 g/l, at least about 0.05 g/l, or at least about 0.1 g/l. The chloride ion component of the media is preferably derived from a chloride salt, with a preferred salt being sodium chloride. Other sources of chloride in the media include potassium chloride and calcium chloride. Sources of chloride ion may include more than one chloride-containing compound in the media, and may include hydrochloric acid which may be used to adjust pH of the media, as well as $MnCl_2$ and $FeCl_3$.

In another aspect of the media of the present invention, the potassium ion concentration is greater than about 0.25 g/L. Potassium ion is generally present at low levels in seawater, being approximately 0.38 g/l seawater. Culture media known in the art for growth of marine microalgae closely follows the composition of seawater, with levels of potassium ion generally being the same or less. For example, Tuttle and Loeblich (1975) disclose 9 mM KCl, which is the equivalent of approximately 0.35 g/l potassium ion. In Handbook of Phycological Methods (Janet R. Stein, Ed., Cambridge University Press, 1973), potassium ion in the media is disclosed to be 9.83 mM as potassium chloride, which is the equivalent of approximately 0.36 g/l potassium ion. In one embodiment, the present invention includes potassium ion at a concentration of greater than about 0.39 g/l. The present inventors have found that, once potassium ion is greater than a threshold level, cultures are relatively insensitive to the precise concentration of potassium ion, growing well and yielding commercially viable levels of DHA at a range of potassium ion concentrations. Preferably, the lower range of potassium ion concentration is at least about 0.2 g/l, at least about 0.25 g/l, at least about 0.3 g/l, at least about 0.35 g/l, at least about 0.4 g/l, at least about 0.45 g/l, at least about 0.5 g/l, at least about 0.6 g/l, and at least about 0.7 g/l. Preferably, the upper range of the potassium ion concentration is at most about 10 g/l, at most about 6 g/l, at most about 4 g/l, at most about 3 g/l, at most about 2.8 g/l, at most about 2.6 g/l, at most about 2.4 g/l, at most about 2.2 g/l, at most about 2 g/l, at most about 1.9 g/l, at most about 1.8 g/l, at most about 1.7 g/l, at most about 1.6 g/l, at most about 1.5 g/l, and at most about 1 g/l. Most preferred concentrations of potassium ion are about 0.75 g/l, 0.8 g/l, 0.85 g/l, 0.9 g/l, and 0.95 g/l. Preferable ranges for potassium ion are between about 0.45 g/l and about 1.5 g/l; more preferably between about 0.5 g/l and about 1.2 g/l; more preferably between about 0.6 g/l and about 1 g/l; even more preferably between about 0.7 g/l and about 0.9 g/l; and most preferably about 0.8 g/l.

The source of potassium ion can be from any potassium salt compatible with cell culture and microalgae of the class Dinophyceae in particular. Potassium ion may be derived from a mixture of salts in the media. Preferred potassium salts include potassium chloride, potassium sulfate, potassium acetate, potassium bicarbonate, potassium phosphate, among others. A preferred source of potassium ion is potassium sulfate.

In one aspect of the present invention, the amount of DHA yield from the cultures at harvest is greater than the amount of DHA yield from cultures not grown in media of the present invention. In one embodiment, the DHA yield using low chloride concentrations using processes of the present invention is at least 0.2 gram DHA per liter of 7-day culture or 0.04 g DHA/$10^9$ cells.

In another aspect of the present invention, the media will also contain additional sources of sodium ion other than sodium chloride. The present inventors have found that sodium ion levels are not critical to the present invention. Cultures of marine organisms of the present invention are relatively insensitive to the precise concentration of sodium ion, growing well and yielding commercially viable levels of DHA at a range of sodium ion concentrations. Many different sources of sodium ion are compatible with the present invention, including sodium sulfate, sodium carbonate, sodium hydrogen carbonate, and sodium acetate. A preferred source of additional sodium ion is sodium sulfate. In a preferred embodiment, the medium contains at least about 1 g/l sodium ion up to about 8 g/l sodium ion. At the lower end of the range, preferred sodium ion concentration is at least about 1 g/l, at least about 1.5 g/l, at least about 2 g/l, and at least about 2.5 g/l. Preferably, the upper range of the sodium ion concentration is at most about 15 g/l, at most about 12 g/l, at most about 10 g/l, at most about 9 g/l, at most about 8 g/l, at most about 7 g/l, at most about 6 g/l, at most about 5.5 g/l, at most about 5 g/l, at most about 4.5 g/l, at most about 4 g/l. Most preferred concentrations of sodium ion are about 2.75 g/l, 3 g/l, 3.25 g/l, 3.5 g/l, and 3.75 g/l. Preferable ranges for sodium ion are between about 1.5 g/l up to about 7.5 g/l, even more preferred is about 2.0 g/l up to about 6 g/l, and even more preferred is more than about 2.5 g/l up to about 5 g/l. In the most preferred embodiments, sodium ion is at least about 3 g/l to about 3.5 g/l. The most preferred level of sodium is about 3.25 g/l. As described previously, the cultures are relatively insensitive to the precise levels of sodium, and therefore even higher levels may be used. However, once sodium levels above about 8 g/l are used, the culture yields begin to drop slightly.

In another embodiment, the present invention includes a method of producing DHA by culturing heterotrophic microalgae of the class Dinophyceae in a culture medium. The medium comprises chloride ion at a concentration of less than or equal to about 2 g/l, potassium ion at a concentration of greater than or equal to about 0.25 g/l and sodium ion present in a ratio of less than or equal to about 27:1 wt:wt sodium:potassium. In this embodiment, the microalgae produces at least about 0.2 g DHA per liter 7 day culture or 0.04 g DHA/$10^9$ cells. In this embodiment, the culture medium contains sodium ion in a ratio with potassium ion of less than or equal to about 27:1, weight:weight. In seawater, the sodium ion to potassium ion ratio is approximately 27.3:1. In other words, the amount of sodium ion is about 27.3 times higher than the amount of potassium ion. In the present invention, the inventors have found that increasing the potassium ion relative to the sodium ion increases the yield of DHA from the culture. A preferred ratio of sodium ion to potassium ion less than or equal to about 27:1, less than or equal to about 25:1, less than or equal to about 23:1, less than or equal to about 21:1, less than or equal to about 19:1. More preferred are ratios of less than or equal to about 17:1, less than or equal to about 15:1, less than or equal to about 13:1, less than or equal to about 11:1. Even more preferred are ratios of less than or equal to about 9:1, less than or equal to about 7:1, or less than or equal to about 5:1. A preferred ratio is about 4:1.

In another embodiment, the present invention includes a method of producing DHA by culturing heterotrophic microalgae of the class Dinophyceae in a culture medium, wherein the culture medium has a pH of less than about 6, and wherein the microalgae produces at least about 0.2 g DHA per liter of 7 day culture or 0.04 g DHA/$10^9$ cells. In a preferred embodiment, the pH is less than or equal to about 5.5, and more preferably less than or equal to about 5. In a preferred embodiment, the pH is less than or equal to about 4.5. In a preferred embodiment, the medium further comprises chloride ion concentration at less than or equal to about 2 g/l, preferably less than or equal to about 1 g/l, even more preferably less than or equal to about 0.3 g/l. The medium also preferably comprises potassium ion at concentrations greater than or equal to about 0.25 g/l, greater than or equal to about 0.4 g/l, and even more preferably is greater than or equal to about 0.8 g/l. Preferably, the source of potassium ion is potassium sulfate. In a preferred embodiment, the medium further comprises a source of sodium ion such that the sodium ion concentration is from about 1 g/l to about 8 g/l. More preferably, the sodium ion is from about 1.5 g/l to about 5 g/l. A preferred source of sodium ion is sodium sulfate. Included in this embodiment is a biomass produced by this method.

In another embodiment, the present invention includes a method for the preparation of low pH tolerant strains of species of the class of Dinophyceae and strains produced thereby. Methods include preparation of low pH media and subculturing the desired Dinophyceae species until the culture produces a desired amount of DHA. Subculturing may be carried out in the following manner. An inoculum of the desired Dinophyceae species is placed in the low pH media and allowed to grow a defined amount of time, preferably 7 days. The amount of time is not critical, but should be chosen such that the strain has sufficient time to grow, but before it reaches senescence. The yield of DHA of the culture is calculated. If less than the desired amount, additional subculturing is performed in the following manner. Fresh low pH media is prepared and inoculated with the low pH cultivated culture, and incubated for an appropriate amount of time. The yield of DHA of the culture is calculated. If the yield of DHA is less than the desired amount, subculturing is repeated until the desired yield of DHA is achieved. A preferred pH to select tolerance for is at or below about 6, more preferably at or below about 5.5, even more preferably at or below about 5, and even more preferably at or below 4.5. Media in which to carry out this method is any culture media known in the art, with the pH adjusted to the desired levels. A preferred media in which to carry out the subculturing is the media described in Example 1.

The present invention also includes a biomass produced by one of the methods of the invention.

Cultivation conditions consistent with the organisms and methods of the present invention may be accomplished by methods known in the art and include the methods disclosed in U.S. Pat. Nos. 5,130,242, 5,407,957, 5,397,591; 5,492,938; and 5,711,983, and optimal conditions may readily be determined by those skilled in the art. Briefly, cultivation may be accomplished in any suitable fermentor, preferably in either a stirred tank fermentor or an air lift fermentor, which provide a source of oxygen to the microorganisms. The agitation of the microorganism should be maintained at a level such that while dissolved oxygen concentrations are sufficient to support the growth of the culture and production of DHA, the agitation does not shear or otherwise damage the microorganisms. Preferred levels of dissolved oxygen are at least 10% of air saturation level. More preferably, levels of dissolved oxygen are maintained from about 10% to about 50% of air saturation levels.

Cultivation may be carried out at any life-sustaining temperature. Generally, microorganisms will grow at temperatures ranging from about 15° C. to about 34° C. Preferably the temperature is maintained at about 20° C. to about 28° C.

The organisms may be harvested by conventional means, known to those of skill in the art, such as centrifugation, flocculation, or filtration, and can be processed immediately or dried for future processing. In either event, lipid may be extracted. As used herein, the term "lipid" includes phospholipids; free fatty acids; esters of fatty acids; triacylglycerols; diacylglycerides; monoacylglycerides; lysophospholipids; soaps; phosphatides; sterols and sterol esters; carotenoids; xanthophylls (e.g., oxycarotenoids); hydrocarbons; and other lipids known to one of ordinary skill in the art. As is well understood by the skilled artisan, the DHA referred to in the present invention can be in the form of these various lipids, and is not limited to the free fatty acid. Different types or components of the lipids can be extracted, depending on the extraction technique that is used. Lipids can be extracted with an effective amount of solvent. Suitable solvents can be determined by those of skill in the art. Polar lipids (e.g., phospholipids) are generally extracted with polar solvents (e.g., chloroform/methanol) and neutral lipids (e.g., triacylglycerols) are generally extracted with nonpolar solvents (e.g., hexane). A preferred solvent is pure hexane. A suitable ratio of hexane to dry biomass is about 4 liters of hexane per kilogram of dry biomass. The hexane preferably is mixed with the biomass in a stirred reaction vessel at a temperature of about 50° C. for about 2 hours. After mixing, the biomass is filtered and separated from the hexane containing the oil. The hexane is removed from the oil by distillation techniques known to those of skill in the art. Conventional oilseed processing equipment is suitable to perform the filtering, separation and distillation. Additional processing steps, known to those of skill in the art, can be performed if required or desirable for a particular application. Alternative methods for lipid recovery are described in the following references which are incorporated by reference herein in their entirety: PCT Publication WO 0176715, entitled "Method for the Fractionation of Oil and Polar Lipid-Containing Native Raw Materials"; PCT Publication WO 0176385, entitled "Method For The Fractionation Of Oil And Polar Lipid-Containing Native Raw Materials Using Alcohol And Centrifugation"; PCT Publication WO 0153512, entitled "Solventless Extraction Process."

The present invention, while disclosed in terms of specific organisms and methods, is intended to include all such methods and strains obtainable and useful according to the teachings disclosed herein, including all such substitutions, modifications, and optimizations as would be available expedients to those of ordinary skill in the art. The following examples and test results are provided for the purposes of illustration and are not intended to limit the scope of the invention.

EXAMPLE 1

This Example describes the preparation of Standard Screening Medium (SSM) with 4.5 g/l NaCl. To prepare the media, the first step includes adding the following compounds to distilled water to 90% of final desired volume as shown in Table 1. All compounds are available from Sigma Aldrich, St. Louis, Mo.

TABLE 1

Amounts and Final Concentrations of media before autoclaving

| Compound | Final Concentration | Amount chloride ion added (g/l) | Amount potassium ion added (g/l) | Amount sodium ion added (g/l) |
|---|---|---|---|---|
| $CaCl_2$—$2H_2O^1$ | 0.3 g/l | 0.09 | | |
| $MgSO_4$—$7H_2O$ | 1.25 g/l | | | |
| NaCl | 4.5 g/l | 3 | | 1.5 |
| MES | 10.7 g/l | | | |
| MSG | 1.5 g/l | | | |
| Tastone 154 | 0.5 g/l | | | |
| $KH_2PO_4$ | 0.014 g/l | | .004 | |
| KCl | 0.14 g/l | 0.067 | 0.073 | |
| $CuSO_4$—$5H_2O$ | $0.15 \times 10^{-3}$ g/l | | | |

TABLE 1-continued

Amounts and Final Concentrations of media before autoclaving

| Compound | Final Concentration | Amount chloride ion added (g/l) | Amount potassium ion added (g/l) | Amount sodium ion added (g/l) |
|---|---|---|---|---|
| $CoCl_2$—$6H_2O$ | $0.3 \times 10^{-3}$ g/l | negligible | | |
| $H_3BO_3$ | $10 \times 10^{-3}$ g/l | | | |
| $MnCl_2$—$4H_2O$ | $4.5 \times 10^{-3}$ g/l | negligible | | |
| $ZnSO_4$—$7H_2O$ | $0.3 \times 10^{-3}$ g/l | | | |
| NaOH (to adjust pH to 6.3) | 1.16 g/l | | | 0.67 |
| $FeCl_2$[2] | $6 \times 10^{-3}$ g/ml | negligible | | |
| Thiamine[3] | $1 \times 10^{-3}$ g/l | | | |
| Biotin[3] | $2 \times 10^{-6}$ g/l | | | |
| glucose[4] | 50 g/l | | | |
| total of each ion | | 3.16 | 0.08 | 2.17 |

[1]Calcium chloride dihydrate is 244 g/mol with 28.7% chloride.
[2]stock solution autoclaved separately and added in a sterile manner to media post-autoclave; made fresh every two weeks.
[3]stock solution filter sterilized through a 0.2 micron filter; stored at 4° C. in the dark. Added in a sterile manner to media post-autoclave.
[4]stock solution autoclaved separately. Added in a sterile manner to media post-autoclave.

Bring autoclaved media up to 100% volume with sterile water. For screening experiments, 35 ml of SSM media is added to sterile 250 ml Erlenmeyer flasks. 1 ml of inoculum is added per flask for an initial cell concentration of $1 \times 10^5$ cells per ml. Inoculum is of 5-6 day old culture. Cultures are grown at 26.5° C. on a rotary shaker at 135 rpm.

EXAMPLE 2

This Example describes the preparation of 1000 ppm chloride ion Screening Medium (SSM) with 1.41 g/l NaCl (that together with calcium chloride and potassium chloride results in approximately 1000 ppm, 1 g/l chloride ion). To prepare the media, the first step includes adding the following compounds to deionized distilled water to 90% of final desired volume as shown in Table 2. All compounds are available from Sigma Aldrich, St. Louis, Mo.

TABLE 2

Amounts and Final Concentrations of media before autoclaving

| Compound | Final Concentration | Amount chloride ion added (g/l) | Amount potassium ion added (g/l) | Amount sodium ion added (g/l) |
|---|---|---|---|---|
| $CaCl_2$—$2H_2O$ | 0.3 g/l | 0.09 | | |
| $MgSO_4$—$7H_2O$ | 1.25 g/l | | | |
| NaCl | 1.41 g/l | 0.85 | | 0.47 |
| MES | 10.7 g/l | | | |
| MSG | 1.5 g/l | | | |
| Tastone 154 | 0.5 g/l | | | |
| $KH_2PO_4$ | 0.014 g/l | | 0.004 | |
| KCl | 0.14 g/l | 0.067 | 0.073 | |
| $CuSO_4$—$5H_2O$ | $0.15 \times 10^{-3}$ g/l | | | |
| $CoCl_2$—$6H_2O$ | $0.3 \times 10^{-3}$ g/l | negligible | | |
| $H_3BO_3$ | $10 \times 10^{-3}$ g/l | | | |
| $MnCl_2$—$4H_2O$ | $4.5 \times 10^{-3}$ g/l | negligible | | |
| $ZnSO_4$—$7H_2O$ | $0.3 \times 10^{-3}$ g/l | | | |
| NaOH (to adjust pH to 6.3) | 1.6 g/l | | | 0.67 |
| $FeCl_2$[1] | $6 \times 10^{-3}$ g/l | negligible | | |
| Thiamine[2] | $1 \times 10^{-3}$ g/l | | | |
| Biotin[2] | $2 \times 10^{-6}$ g/l | | | |
| glucose[3] | 50 g/l | | | |
| total of each ion | | 1.00 | 0.08 | 1.14 |

[1]stock solution autoclaved separately and added in a sterile manner to media post-autoclave; made fresh every two weeks.
[2]stock solution filter sterilized through a 0.2 micron filter; stored at 4° C. in the dark. Added in a sterile manner to media post-autoclave.
[3]stock solution autoclaved separately. Added in a sterile manner to media post-autoclave.

Bring autoclaved media up to 100% volume with sterile water. For screening experiments, 35 ml of SSM media is added to sterile 250 ml Erlenmeyer flasks. 1 ml of inoculum is added per flask for an initial cell concentration of $1 \times 10^5$ cells per ml. Inoculum is of 5-6 day old culture. Cultures are grown at 26.5° C. on a rotary shaker at 135 rpm.

EXAMPLE 3

This Example describes the preparation of 300 ppm chloride ion Screening Medium (SSM) with 0.211 g/l NaCl (that together with calcium chloride and potassium chloride results in 0.3 g/l chloride ion). To prepare the media, the first step includes adding the following compounds to deionized distilled water to 90% of final desired volume as shown in Table 3. All compounds are available from Sigma Aldrich, St. Louis, Mo.

TABLE 3

Amounts and Final Concentrations of media before autoclaving

| Compound | Final Concentration | Amount chloride ion added (g/l) | Amount potassium ion added (g/l) | Amount sodium ion added (g/l) |
|---|---|---|---|---|
| CaCl$_2$—2H$_2$O | 0.3 g/l | 0.09 | | |
| MgSO$_4$—7H$_2$O | 1.25 g/l | | | |
| NaCl | 0.211 g/l | 0.13 | | 0.07 |
| MES | 10.7 g/l | | | |
| MSG | 1.5 g/l | | | |
| Tastone 154 | 0.5 g/l | | | |
| KH$_2$PO$_4$ | 0.014 g/l | | 0.004 | |
| KCl | 0.14 g/l | 0.067 | 0.073 | |
| CuSO$_4$—5H$_2$O | $0.15 \times 10^{-3}$ g/l | | | |
| CoCl$_2$—6H$_2$O | $0.3 \times 10^{-3}$ g/l | negligible | | |
| H$_3$BO$_3$ | $10 \times 10^{-3}$ g/l | | | |
| MnCl$_2$—4H$_2$O | $4.5 \times 10^{-3}$ g/l | negligible | | |
| ZnSO$_4$—7H$_2$O | $0.3 \times 10^{-3}$ g/l | | | |
| NaOH (to adjust pH to 6.3) | 1.16 g/l | | | 0.67 |
| FeCl$_2$[1] | $6 \times 10^{-3}$ g/l | negligible | | |
| Thiamine[2] | $1 \times 10^{-3}$ g/l | | | |
| Biotin[2] | $2 \times 10^{-6}$ g/l | | | |
| glucose[3] | 50 g/l | | | |
| total of each ion | | 0.30 | 0.08 | 0.74 |

[1]stock solution autoclaved separately and added in a sterile manner to media post-autoclave; made fresh every two weeks.
[2]stock solution filter sterilized through a 0.2 micron filter; stored at 4° C. in the dark. Added in a sterile manner to media post-autoclave.
[3]stock solution autoclaved separately. Added in a sterile manner to media post-autoclave.

Bring autoclaved media up to 100% volume with sterile water. For screening experiments, 35 ml of SSM media is added to sterile 250 ml Erlenmeyer flasks. 1 ml of inoculum is added per flask for an initial cell concentration of $1 \times 10^5$ cells per ml. Inoculum is of 5-6 day old culture. Cultures are grown at 26.5° C. on a rotary shaker at 135 rpm.

EXAMPLE 4

This Example describes the procedure for Growth and Harvest of *Crypthecodinium cohnii* in pH 6.3 SSM.

SSM media was prepared as described in one of Examples 1-3, depending on which media was being tested. Additional media components were prepared and added to a media as described in Examples 1-3. All steps prior to harvest were carried out in sterile conditions.

To prepare the inoculum culture, the following procedures were used. To a 250 ml Erlenmeyer flask, 49 ml of SSM (described in Example 1) were added to a 250 ml Erlenmeyer flask. 1 ml of a five day old culture of *C. cohnii* Strain T-HF (Strain T-HF identifies the organism ATCC 40750 that has been repeatedly cultured) was added. The culture flask was placed on a shaker rotating at 135 rpm in a 27° C. incubator with no lights. After three days of growth, the culture is moved to a sterile hood and 1 ml is removed and counted using a Coulter Counter (Coulter Z2 Particle Count and Size Analyzer, obtained from Beckman Coulter, Inc.). The cell count is used to calculate the amount of the inoculum culture that must be used to start a new 50 ml culture at a cell density of $1.0 \times 10^5$ cells per ml.

To test the different media components, an appropriate media was prepared as described below and introduced into a sterile 250 ml Erlenmeyer flask. The amount of inoculum as previously calculated was transferred into the culture flask containing the media prepared in the Erlenmeyer flask. The culture flask was placed on a shaker rotating at 135 rpm in a 27° C. incubator with no lights. After seven days of growth, the culture was harvested as follows.

A 50 ml centrifuge tube (obtained from VWR Scientific) was labeled and weighed for each culture. Another 50 ml centrifuge tube was labeled, but not weighed, for each culture. The culture was then poured into the labeled 50 ml tube. Volumes were recorded and cell counts performed with the Coulter Z2 Particle Count and Size Analyzer. The pH was measured.

Half the culture was poured into the tared 50 ml tube, and a 70% solution of isopropyl rubbing alcohol (IPA) was added to bring the total volume in the tube to 50 ml. The culture was mixed by inverting the tube two to three times. The culture was then centrifuged at 4000 rpm for five minutes using a Sorvall General Purpose RC-3 Centrifuge. The supernatant was poured off. The other half of the culture was poured on top of the pellet and the steps were repeated starting with the 70% solution of the IPA. The pellet was then washed two times with 39% IPA using the following procedure: to cell pellet, add 35 mL 39% IPA; vortex the tube (using a Vortex Genie-2 from VWR Scientific) at full speed for 10 seconds; after collection, the pellet was then freeze-dried for at least 48 hours.

The tube containing the pellet (biomass) was weighed and the dry weight of the biomass was calculated. Dry weight was calculated as follows: determine the weight of the tube containing the biomass minus the tare weight of the tube. Divide this number by the recorded volume of culture at harvest, divided by 1000.

Fatty acid composition (and % DHA) may be determined according to procedures disclosed in Morrison and Smith, "Preparation of Fatty Acid Methyl Esters and Dimethylacetals from Lipids with Boron Fluoride-Methanol", Journal of Lipid Research, Vo. 5, 1964, and the American Oil Chemist's Society Official Methods used to quantitate long chain fatty acids and eicosapentaenoic acid (EPA) and DHA in marine oils (Method Celb-89). Briefly, the samples are mixed with standard amounts of oil (internal standards), saponified with 0.5 N methanolic sodium hydroxide, and derivatized with boron trifluoride/methanol. The fatty acid methyl esters are extracted and analyzed on a gas chromatograph with flame ionization detector (Hewlett Packard 5890 Series II Plus gas chromatograph using a 30 m×0.25 mm×0.25 μm Restek FAMEWAX #12497 column).

EXAMPLE 5

This Example describes the growth of *C. cohnii* and the production of DHA at low NaCl levels using prior art media.

One liter of SSM not containing NaCl was made and autoclaved. Four stocks of concentrated NaCl were prepared (135 g/l, 90 g/l, 45 g/l, and 22.5 g/l). To each shake flask containing 48.75 ml of SSM minus NaCl media and 1.25 ml of the appropriate NaCl stock was added. Two controls were set up: 4.5 g/l NaCl using normal SSM as described in Example 1, and no NaCl using SSM with no added NaCl. Duplicates of each NaCl level were used.

Growth and harvest was performed as described in Example 4. Table 5 describes the results of this Example. All numbers are given as an average of two cultures.

TABLE 5

Biomass, % DHA, % Fat, and DHA yield for *C. cohnii* grown in SSM containing lowered amounts of NaCl.

| g/l NaCl | g/l chloride ion[1] | biomass dry weight g/l | % DHA in fat (wt/wt) | % fat in biomass (wt/wt) |
|---|---|---|---|---|
| 4.5 | 2.73 | 3.53 | 51.63 | 52.45 |
| 3.38 | 2.05 | 3.66 | 51.55 | 47.83 |
| 2.25 | 1.37 | 3.85 | 52.19 | 48.40 |
| 1.73 | 0.68 | 2.73 | 54.65 | 54.59 |
| 0.56 | 0.34 | 2.70 | 55.48 | 48.81 |
| 0 | 0 | 1.99 | 51.00 | 34.19 |

[1]Reflects amount of chloride ion (0.20 g/l) from sodium chloride only. See Examples 1-3.

Table 5 shows the yield of biomass, % fat, and DHA yield for *C. cohnii* grown in SSM containing lowered amounts of NaCl. It can be seen that as the amount of NaCl added into the culture decreases, both biomass yield and fat levels decreased, resulting in a lowered yield of DHA.

EXAMPLE 6

This Example describes the yield of DHA achieved with 4.5 g/l NaCl in the culture medium described in Example 1.

Cultures were grown as described in Example 4. Table 6 shows the results of this example

TABLE 6

Biomass, % DHA, % Fat, and DHA yield for *C. cohnii* grown in SSM of Example 1

| (g/l) sodium chloride | (g/l) sodium sulfate | (g/l) chloride[1] ion | (g/l) sodium ion | % DHA in fat (wt/wt) | % fat in biomass (wt/wt) | biomass dry weight (g/l) |
|---|---|---|---|---|---|---|
| 4.5 g/l | | 2.73 | 1.77 | 53.9 | 65.03 | 3.1 |

[1]Reflects amount of chloride ion from sodium chloride only

EXAMPLE 7

This Example describes enhanced growth of *C. cohnii* and production of DHA in low chloride media using various concentrations of potassium ion and sodium ion in the form of potassium sulfate and sodium sulfate.

Low chloride SSM was prepared in the manner described in Example 3, using 0.18 g/l calcium acetate and omitting calcium chloride and potassium chloride. Every possible combination of $K_2SO_4$ concentrations of 0.16 g/l, 0.80 g/l, 1.6 g/l, 3.2 g/l, and 4.8 g/l were tested against $Na_2SO_4$ concentrations of 4.9 g/l, 9.8 g/l, 14.7 g/l, 19.6 g/l, and 24.5 g/l using a two dimensional matrix. All cultures were grown as described in Example 4. The results are presented in Table 7.

TABLE 7

Comparison of the biomass, % DHA, % Fat, and DHA yield obtained for *C. cohnii* grown in media with varying concentrations of potassium sulfate and sodium sulfate

| Flask | g/L $K_2SO_4$ | g/L $Na_2SO_4$ | Sodium ion[1] (g/l) | Potassium ion (g/l) | DW g/L | % DHA in fat (wt/wt) | % Fat in biomass (wt/wt) |
|---|---|---|---|---|---|---|---|
| 1 | 0.16 | 4.90 | 1.77 | 0.07 | 2.55 | 57.97 | 60.80 |
| 2 | 0.16 | 9.80 | 3.35 | 0.07 | 1.53 | 52.39 | 41.45 |
| 3 | 0.16 | 14.70 | 4.93 | 0.07 | — | — | — |
| 4 | 0.16 | 19.60 | 6.53 | 0.07 | 0.75 | 42.88 | 13.28 |
| 5 | 0.16 | 24.50 | 8.11 | 0.07 | 0.71 | 41.46 | 12.11 |
| 6 | 0.80 | 4.90 | 1.77 | 0.36 | 3.79 | 56.76 | 63.19 |
| 7 | 0.80 | 9.80 | 3.35 | 0.36 | 4.03 | 55.11 | 64.96 |
| 8 | 0.80 | 14.70 | 4.93 | 0.36 | 3.66 | 55.14 | 64.39 |
| 9 | 0.80 | 19.60 | 6.52 | 0.36 | 3.07 | 56.88 | 58.12 |
| 10 | 0.80 | 24.50 | 8.11 | 0.36 | 2.91 | 57.37 | 53.65 |
| 11 | 1.60 | 4.90 | 1.77 | 0.72 | 3.74 | 55.90 | 63.46 |
| 12 | 1.60 | 9.80 | 3.35 | 0.72 | 3.83 | 55.00 | 65.43 |
| 13 | 1.60 | 14.70 | 4.93 | 0.72 | 3.49 | 56.48 | 60.09 |
| 14 | 1.60 | 19.60 | 6.53 | 0.72 | 3.18 | 54.71 | 54.92 |
| 15 | 1.60 | 24.50 | 8.11 | 0.72 | 2.83 | 54.82 | 49.02 |
| 16 | 3.20 | 4.90 | 1.77 | 1.44 | 3.51 | 54.42 | 63.99 |
| 17 | 3.20 | 9.80 | 3.35 | 1.44 | 3.36 | 55.40 | 61.12 |
| 18 | 3.20 | 14.70 | 4.93 | 1.44 | 3.40 | 55.61 | 59.34 |
| 19 | 3.20 | 19.60 | 6.53 | 1.44 | 3.07 | 57.07 | 59.44 |
| 20 | 3.20 | 24.50 | 8.11 | 1.44 | 2.77 | 57.00 | 57.07 |
| 21 | 4.80 | 4.90 | 1.77 | 2.15 | 2.82 | 54.94 | 57.43 |
| 22 | 4.80 | 9.80 | 3.35 | 2.15 | 2.81 | 53.97 | 58.12 |
| 23 | 4.80 | 14.70 | 4.93 | 2.15 | 2.94 | 54.26 | 58.75 |
| 24 | 4.80 | 19.60 | 6.52 | 2.15 | 2.82 | 55.53 | 56.88 |
| 25 | 4.80 | 24.50 | 8.11 | 2.15 | 2.50 | 57.02 | 53.00 |

[1]Includes sodium ion added by 0.45 g/l sodium chloride or 0.18 g/l sodium ion.

The results shown in Table 7 indicate that increased potassium levels caused the growth and yield of DHA for *C. cohnii* to be comparable to that achieved at high chloride levels. The enhancement effect in this Example appeared at 0.8 g/l potassium sulfate, the second-lowest level tested, and thereafter was relatively insensitive to the amounts of potassium sulfate.

At the highest levels of potassium sulfate tested, 4.8 g/l, there appeared to be a slight decline in yield. Growth and DHA yield also appeared relatively insensitive to the amount of sodium sulfate used, however, growth and yield dropped slightly as increasing amounts of sodium sulfate were used, starting at about 19.6 g/l sodium sulfate. The best combinations based on the amount of DHA in g/L were those using: 0.8 g/L $K_2SO_4$ and 9.8 g/L $Na_2SO_4$, representing a 5× increase of potassium and a 2× increase of sodium over the normal Low Chloride-SSM (described in Example 3); and 1.6 g/L $K_2SO_4$ and 9.8 g/L $Na_2SO_4$, representing a 10× increase of potassium and a 2× increase of sodium over the normal Low chloride-SSM (described in Example 3).

EXAMPLE 8

This Example demonstrates enhancement of growth of *C. cohnii* and production of DHA using media containing a range of potassium sulfate, 0.32 g/l, 0.64 g/l, 0.96 g/l, 1.28 g/l, 1.60 g/l, and 1.9 g/l and sodium sulfate at 4.9 g/l and 9.8 g/l.

Low chloride SSM was prepared in the manner described in Example 7, and all cultures were grown as described in Example 4. The results are presented in Table 8.

TABLE 8

Comparison of the biomass, % DHA, % Fat, and DHA yield obtained for *C. cohnii* grown in media with varying concentrations of potassium sulfate and sodium sulfate

| Flask | g/L $K_2SO_4$ | g/L $Na_2SO_4$ | DW g/L | % DHA in fat (wt/wt) | % Fat in biomass (wt/wt) | Sodium ion[1] (g/l) | Potassium ion (g/l) |
|---|---|---|---|---|---|---|---|
| 1 | 0.32 | 4.90 | 3.22 | 57.76 | 75.22 | 1.77 | 0.14 |
| 2 | 0.32 | 9.80 | 3.05 | 57.61 | 66.15 | 3.35 | 0.14 |
| 3 | 0.64 | 4.90 | 3.49 | 58.66 | 61.45 | 1.77 | 0.29 |
| 4 | 0.64 | 9.80 | 3.47 | 58.50 | 63.22 | 3.35 | 0.29 |
| 5 | 0.96 | 4.90 | 3.43 | 58.45 | 59.98 | 1.77 | 0.43 |
| 6 | 0.96 | 9.80 | 3.66 | 51.91 | 58.03 | 3.35 | 0.43 |
| 7 | 1.28 | 4.90 | 3.51 | 58.72 | 58.67 | 1.77 | 0.57 |
| 8 | 1.28 | 9.80 | 3.67 | 56.93 | 75.09 | 3.35 | 0.57 |
| 9 | 1.60 | 4.90 | 3.32 | 57.16 | 65.76 | 1.77 | 0.72 |
| 10 | 1.60 | 9.80 | 3.57 | 56.89 | 62.11 | 3.35 | 0.72 |
| 11 | 1.90 | 4.90 | 3.36 | 56.15 | 59.95 | 1.77 | 0.85 |
| 12 | 1.90 | 9.80 | 3.54 | 54.74 | 60.42 | 3.35 | 0.085 |

[1]Includes sodium ion added by 0.45 g/l sodium chloride or 0.18 g/l sodium ion.

Results shown in Table 8 showed that the optimum DHA yield occurs with concentrations of $K_2SO_4$ at 1.28 g/L and 9.8 g/L $Na_2SO_4$. The results shown in Table 8 indicate that the effect of additional potassium can be seen at potassium sulfate levels as low as 0.32 g/l and appear relatively constant through 1.90 g/l. Growth and yield are relatively insensitive to sodium sulfate levels of 4.9 g/l or 9.8 g/l.

EXAMPLE 9

The following Example describes subculturing *C. cohnii* to obtain a strain that is adapted to growth at pH 5.

*C. cohnii* Strain T-HF was cultured in shake flasks in the manner described in Example 4, in media described in Example 1, except that the pH of the media upon the start of culture was pH 5. After 7 days, an inoculum from the culture was used to start a new culture at pH 5 under the same conditions. Initially the growth at pH 5 was slow, but after multiple transfers, the DHA yield began to improve and over time has approached the yield seen from cultures grown at pH 6.3, resulting in a low pH strain. See FIG. 1. It was noted that the pH of the culture at the end of the 7 day growth period was 5.4. Attempts to adapt the strain using buffers citrate, malate, acetate, and lactate were unsuccessful due to those buffer's toxic effect on Strain T-HF.

The low pH strain was then grown in the pH 5 media described above, but pH was kept at 5.0. The low pH adapted strain grew equally well at pH 5 and at pH 5.4.

EXAMPLE 10

The following Example describes a comparison of DHA yields from *C. cohnii* Strain T-HF grown at pH 6.3 and 2730 ppm chloride ion media and the low pH strain at pH 5 in 1000 ppm chloride ion media.

*C. cohnii* Strain T-HF was grown as described in Example 4 in media as described in Example 1. *C. cohnii* strain was grown in low chloride media as described in Example 2, with potassium sulfate and sodium sulfate added. Each experiment was run in duplicate, and all flasks were harvested daily to determine the kinetics of DHA yield. The results are shown in FIG. 1. FIG. 1 shows that the kinetics of DHA yield were nearly identical under the two different media conditions.

EXAMPLE 11

The following Example describes efforts to adapt *C. cohnii* Strain T-HF to growth at pH 4.5 in 2730 ppm chloride ion medium.

*C. cohnii* Strain T-HF was grown in the manner described in Example 10, with the exception that the media was adjusted to pH 4.5 and half of the MSG was replaced with lysine, while maintaining a constant level of organic nitrogen in the media.

After repeated culturing, yields of DHA of about one-third of yields seen at pH 5 or pH 6.3 were obtained.

EXAMPLE 12

The following Example describes efforts to define conditions for *C. cohnii* growth and DHA yields at pH 4.5 by manipulating potassium concentrations.

A. Factorial experiments were performed at pH 4.5 at 2.73 g/l chloride ion to assess the effect of potassium ion (0.16 g/l to 3.2 g/l). The results showed that higher levels of potassium ion increased the DHA yield to approximately two-thirds of yields obtained for *C. cohnii* at pH 6.3 with the media as described in Example 1.

B. A factorial experiment was run in the manner described in Part A, above, with the exception that the chloride ion levels were held constant at 1.0 g/l. The results showed that higher levels of potassium ion increased the DHA yield to approximately two-thirds of yields obtained for *C. cohnii* grown at pH 6.3 with the media as described in Example 1. The DHA yields obtained at 2.73 g/l chloride ion (described in Part A, above) and at 1.0 g/l chloride ion were comparable.

EXAMPLE 13

This Example describes a time course experiment comparing yields of DHA obtained using the pH 4.5 strain described in Example 12 and Strain T-HF at pH 6.3, 1.0 g/l chloride ion.

The pH 4.5 strain of Example 12 was grown in low chloride, pH 4.5 media as specified in Table 9 in shake flasks after the manner described in Example 4. *C. cohnii* Strain T-HF was grown in the manner described in Example 4 using the media described in Example 1. Inoculum for the pH 4.5 experiment was prepared at pH 4.5, and amounts of inoculum were estimated due to clumping of the cells at pH 4.5.

TABLE 9

Low chloride, pH 4.5 media

| Compound | Final Concentration | Amount chloride ion added (g/l) | Amount potassium ion added (g/l) | Amount sodium ion added (g/l) |
|---|---|---|---|---|
| $CaCl_2$—$2H_2O$ | 0.3 g/l | 0.09 | | |
| $MgSO_4$—$7H_2O$ | 1.25 g/l | | | |
| NaCl | 1.41 | 0.86 | | 0.55 |
| MES | 10.7 g/l | | | |
| MSG | 0.75 g/l | | | |
| Tastone 154 | 0.5 g/l | | | |
| Lysine-HCl | 0.37 | | | |
| $KH_2PO_4$ | 0.014 g/l | | 0.004 | |
| $K_2SO_4$ | 0.15 | | 0.07 | |
| $Na_2SO_4$ | 3.46 | | | 1.12 |
| $CuSO_4$—$5H_2O$ | $0.15 \times 10^{-3}$ g/l | | | |
| $H_3BO_3$ | $10 \times 10^{-3}$ g/l | | | |
| $MnCl_2$—$4H_2O$ | $4.5 \times 10^{-3}$ g/l | negligible | | |
| $ZnSO_4$—$7H_2O$ | $0.3 \times 10^{-3}$ g/l | | | |
| NaOH (to adjust pH to 6.3) | 1.16 g/l | | | 0.67 |
| $FeCl_2$[1] | $6 \times 10^{-3}$ g/l | negligible | | |
| Thiamine[2] | $1 \times 10^{-3}$ g/l | | | |
| Biotin[2] | $2 \times 10^{-6}$ g/l | | | |
| glucose[3] | 50 g/l | | | |
| total of each ion | | 0.30 | 0.08 | 0.74 |

Figure 2:
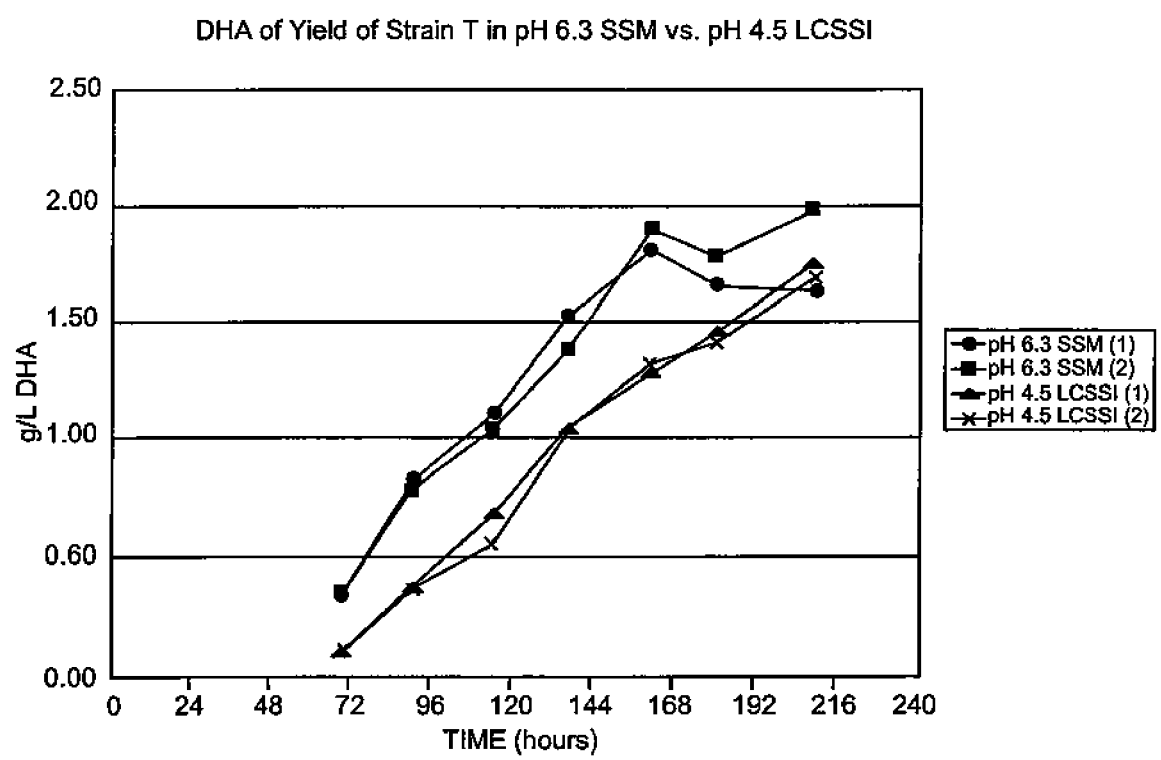
FIG. 2 is a graphical representation of a time course of DHA yield for duplicates of C. cohnii strain T-HF grown at pH 6.3 and 3 g/l chloride ion (denoted pH 6.3 SSM) and C. cohnii strain T-HF, adapted to low pH, grown at pH 4.5 and 1 g/l chloride ion (denoted pH 5.0 LCSSI).

Flasks were harvested daily to determine the kinetics of the DHA yield. The results of the experiment (FIG. 2) indicated that the DHA yield at pH 4.5 was always lower than at pH 6.3, but the rate of increase in the DHA yield as a function of time was about the same at each pH. This suggests that at pH 4.5 the culture is able to accumulate DHA at the same rate as the culture at pH 6.3, however, a lag existed in the DHA yield in cultures grown at pH 4.5 compared to pH 6.3.

This result shows that given extra time, i.e. approximately 24 hours, the DHA yield at pH 4.5 was the same as at pH 6.3. It was not clear whether the lag was caused by a delay in the DHA accumulation at pH 4.5, and as a result, the pH 4.5 culture always had a DHA yield that was lower than the pH 6.3 culture of the same age, or whether the lag was caused by the pH 4.5 culture not receiving an equivalent amount of inoculum. At pH 4.5, the Strain T-HF cells clump such that it is not possible to get an accurate cell count of the culture, and the amount of inoculum to use must be estimated. Therefore, it is possible that the pH 4.5 culture received less inoculum and therefore caused an apparent lag in the kinetics of DHA yield.

Regardless, these data indicated that by using the low pH adapted *C. cohnii* strain and the instant culture media at pH 4.5, the same DHA yield can be achieved as the culture medium at pH 6.3, if culturing time is extended.

EXAMPLE 14

Further optimization of the ion concentrations described in Example 13 above and further subculturing of *C. cohnii* Strain T-HF which has been adapted to pH 5, using techniques described in Example 10, are carried out to decrease the lag time, resulting in 7-day DHA yields at pH 4.5 which are comparable to the yields obtained for *C. cohnii* grown at pH 6.3 with the media as described in Example 1.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

We claim:

1. A method for reducing corrosion of a fermentor during growth of microorganisms in a saline fermentation medium, said method comprising:
    culturing a heterotrophic microalga in a culture medium, wherein the culture medium comprises: (a) chloride ion at a concentration of less than or equal to 2 g/L; and (b) potassium ion at a concentration of greater than or equal to 0.5 g/L; wherein the microalga produces at least 0.04 g DHA per $10^9$ cells.

2. The method of claim 1, wherein the microalga is of the class Dinophyceae.

3. The method of claim 1, wherein the microalga is of the genus *Crypthecodinium*.

4. The method of claim 1, wherein the microalga is of the species *Crypthecodinium cohnii*.

5. The method of claim 1, wherein the concentration of chloride ion is less than or equal to 1 g/L.

6. The method of claim 1, wherein the concentration of chloride ion is less than or equal to 0.3 g/L.

7. The method of claim 1, wherein the concentration of potassium ion is greater than or equal to 0.8 g/L.

8. The method of claim 1, wherein a source of potassium ion comprises potassium sulfate.

9. The method of claim 1, wherein the medium further comprises sodium ion at a concentration of 1 g/L to 8 g/L.

10. The method of claim 9, wherein the concentration of sodium ion is 1.5 g/L to 5 g/L.

11. The method of claim 9, wherein a source of sodium ion comprises sodium sulfate.

12. The method of claim 1, wherein the microalga produces at least 0.10 g docosahexaenoic acid (DHA) per $10^9$ cells.

13. The method of claim 1, wherein the microalga produces at least about 0.20 g DHA per $10^9$ cells.

14. The method of claim 1, further comprising recovering a DHA-containing lipid from the microalga.

15. The method of claim 1, wherein the culture medium has a pH of less than 6.

16. The method of claim 15, wherein the pH is less than or equal to 5.5.

17. The method of claim 15, wherein the pH is less than or equal to 5.

18. The method of claim 15, wherein the pH is less than or equal to about 4.5.

* * * * *

(12) INTER PARTES REEXAMINATION CERTIFICATE (822nd)
United States Patent
Behrens et al.

(10) Number: US 7,829,129 C1
(45) Certificate Issued: Feb. 10, 2014

(54) METHOD TO REDUCE CORROSION DURING FERMENTATION OF MICROALGAE

(75) Inventors: Paul W. Behrens, Ellicot City, MD (US); John M. Thompson, Baltimore, MD (US); Kirk Apt, Ellicot City, MD (US); Joseph W. Pfeifer, III, Reisterstown, MD (US); James P. Wynn, Columbia, MD (US); James Casey Lippmeier, Columbia, MD (US); Jaouad Fichtall, Lexington, KY (US); Jon Hansen, Lexington, KY (US)

(73) Assignee: DSM IP Assets B.V., Heerlen (NL)

Reexamination Request:
No. 95/002,137, Sep. 11, 2012

Reexamination Certificate for:
Patent No.: 7,829,129
Issued: Nov. 9, 2010
Appl. No.: 11/738,416
Filed: Apr. 20, 2007

Related U.S. Application Data

(60) Continuation of application No. 11/313,524, filed on Dec. 20, 2005, now Pat. No. 7,252,979, which is a division of application No. 10/957,075, filed on Oct. 1, 2004, now Pat. No. 7,163,811.

(60) Provisional application No. 60/508,505, filed on Oct. 2, 2003.

(51) Int. Cl.
*C11B 1/00* (2006.01)
*A23D 9/00* (2006.01)
*C12N 1/12* (2006.01)
*C12P 7/64* (2006.01)
*A61K 36/02* (2006.01)

(52) U.S. Cl.
CPC ............... *A61K 36/02* (2013.01); *C12P 7/6427* (2013.01); *C12P 7/6472* (2013.01); *C12P 7/6409* (2013.01)
USPC ......... 426/417; 435/257.1; 435/134; 426/601

(58) Field of Classification Search
None
See application file for complete search history.

(56) References Cited

To view the complete listing of prior art documents cited during the proceeding for Reexamination Control Number 95/002,137, please refer to the USPTO's public Patent Application Information Retrieval (PAIR) system under the Display References tab.

*Primary Examiner* — Evelyn Huang

(57) ABSTRACT

Methods for production of highly unsaturated fatty acids by marine microorganisms, including the heterotrophic marine dinoflagellate Crypthecodinium, using low levels of chloride ion are disclosed. Specifically, methods of increasing production of highly unsaturated fatty acids by marine microorganisms while growing in low chloride media by manipulating sodium ion and potassium ion levels. The invention also relates to methods of production of highly unsaturated fatty acids by marine organisms at low pH levels, and includes methods for generation of low pH tolerant strains.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-18 are cancelled.

\* \* \* \* \*